United States Patent
Samsel et al.

(12)

(10) Patent No.: US 6,444,867 B1
(45) Date of Patent: Sep. 3, 2002

(54) PROCESS FOR LINEAR ALPHA OLEFINS

(75) Inventors: Edward G. Samsel, Baton Rouge, LA (US); Franke N. Brooks, Batavia, IL (US)

(73) Assignee: BP Corporation North America Inc., Chicago, IL (US)

( * ) Notice: Subject to any disclaimer, the term of this patent is extended or adjusted under 35 U.S.C. 154(b) by 0 days.

(21) Appl. No.: 09/860,173

(22) Filed: May 17, 2001

(51) Int. Cl.⁷ .................................................. C07C 2/88
(52) U.S. Cl. ........................................ 585/637; 585/318
(58) Field of Search ................................. 585/328, 637

(56) References Cited

U.S. PATENT DOCUMENTS 4,918,254 A * 4/1990 Diefenbach et al. ........ 556/187
5,210,338 A * 5/1993 Samsel ....................... 526/943
5,276,220 A * 1/1994 Samsel et al. .............. 556/190

* cited by examiner

Primary Examiner—Thuan D. Dang
(74) Attorney, Agent, or Firm—Joseph DiSalvo

(57) ABSTRACT

Linear alpha olefins are typically produced by starting with a trialkylaluminum compound, such as triethylaluminum, and then subjecting the trialkylaluminum compound to alkyl chain growth conditions in the presence of ethylene and elevated temperature and pressure, frequently in the presence of a chain growth catalyst. Under such alkyl chain growth conditions, the alkyl groups attached to the aluminum may be extended by two carbon atoms per reaction with ethylene. The process is permitted to continue until the alkyl groups have reached the desired length at which point they are displaced from the trialkylaluminum compund as alpha olefins, usually in the presence of an excess of ethylene and a displacement catalyst. This invention discloses a new chain growth catalyst system comprising, in combination, non-bridged metallocenes and aluminum complexes having amidinate ligands and inert anions.

9 Claims, No Drawings

PROCESS FOR LINEAR ALPHA OLEFINS

RELATIONSHIP TO PRIOR APPLICATIONS (Not Applicable)

STATEMENT REGARDING FEDERALLY FUNDED RESEARCH (Not Applicable)

FIELD OF THE INVENTION

The invention generally relates to production of linear alpha olefin (LAO) products by the well-known process of carbon chain growth of the alkyl groups in aluminum alkyls and subsequent displacement of the alkyl groups as LAO's. More specifically, this application discloses novel catalysts for use in the chain growth step of the process.

BRIEF DESCRIPTION OF THE INVENTION

The production of linear alpha olefin (LAO) products by the process of carbon chain growth of low carbon count alkyl groups of aluminum trialkyls and subsequent displacement of the lengthened alkyl groups as linear alpha olefins is well known. Typically, LAO products having a carbon atom count in the range of $C_4$–$C_{30}$ are produced by this process and may consist of an odd or even number of carbon atoms. In the chain growth step of the process, the attached alkyl group or groups of a trialkylaluminum compound are typically extended two carbon atoms at a time by subjecting the trialkylaluminum compound to a sufficient amount of ethylene under chain growth conditions. The chain growth step of the process is typically conducted under elevated pressure and temperature. After sufficient chain lengthening of the attached alkyl groups, the alkyl groups are thermally displaced as LAO products from the trialkyl aluminum compound, typically in the presence of excess ethylene. Typically, the displaced LAO products are separated from the reaction mixture. The remainder of the reaction mixture, predominantly comprised of triethyl aluminum and ethylene, is typically recycled to the alkyl chain growth reactor.

Production of LAO products via this method is an important industrial process and substantial resources have been and continue to be expended on improvements to the process. For example, chain growth catalysts consisting of Group 4 and Actinide metallocenes are described in U.S. Pat. Nos. 5,210,338 and 5,276,220, respectively. These metallocenes use co-catalysts consisting of methylaluminoxane (MAO) or of perfluorophenylborate salts of the activating cations N,N-dimethylanilinium and triphenylcabenium. Additionally, the use of displacement catalysts, such as nickel salts, was perfected by the addition of lead catalyst killing agents described in U.S. Pat. No. 4,918,254. Killing the catalyst immediately after the olefin displacement reaction prevents isomerization of the alpha-olefins to internal olefins. This invention represents a continuation of the improvements and discloses a new catalyst system for use in the chain growth step of the process. The new catalyst system comprises in combination a metallocene catalyst and a co-catalyst of cationic aluminum complexes having an amidinate ligand and an inert anion.

DETAILED DESCRIPTION OF THE INVENTION

For the sake of clarity, the term "comprising" as used in this application and the appended claims is defined as "specifying the presence of stated features, integers, steps, or components as recited, but not precluding the presence or addition of one or more other steps, components, or groups thereof". Comprising is different from "consisting of" which does preclude the presence or addition of one or more other steps, components, or groups thereof.

This invention relates to the preparation of linear alpha olefins (LAO's). More particularly, this invention pertains to a novel process for the synthesis of a full range of straight chain alpha olefins by a process which involves the growth of a low molecular weight olefin onto a low molecular weight aluminum alkyl so as to produce a range of aluminum alkyls having the desired $C_4$–$C_{30}$ alkyl chain lengths. Subsequently, the desired olefins are produced therefrom by displacement of the chain-lengthened alkyl groups from the aluminum alkyl.

The method of preparing a full range of $C_4$–$C_{30}$ LAO's is achieved by a process comprising the steps of: (1) adding or growing ethylene onto a low molecular weight, i.e., $C_2$–$C_6$, aluminum trialkyl(s), (2) reacting said grown higher aluminum trialkyls with low molecular weight olefins to obtain a displacement of the higher molecular weight alkyl groups by said lower olefins thus forming higher olefins and lower molecular weight aluminum trialkyls corresponding to the displacing olefins, and (3) separating the desired displaced higher molecular weight olefins as product from the lower molecular weight aluminum alkyls and the remainder of the reaction mixture.

In Step 1 of the above process, it is typical to start with triethyl aluminum or tri(n-propyl) aluminum. The reaction for triethyl aluminum as the feed reacting with ethylene is shown by Equation 1 below.

$$Al(C_2H_5)_3 + C_2H_4 \Rightarrow Al(C_4H_9)(C_2H_5)_2 \qquad \text{Equation 1.}$$

The product of Equation 1 may further react with ethylene, causing all three alkyls to become butyl groups, or it may further react with ethylene so as to change the one butyl group to a hexyl group. Regardless of the manner, the net result of the continued reaction of the feed and the intermediate products will result in an aluminum trialkyl having higher carbon count alkyl groups than the feed aluminum trialkyl. After growth, the alkyl groups in any aluminum trialkyl may be the same or different. Generally, Step 1 of the above process is conducted in the presence of a chain growth catalyst, and typically under elevated temperature and pressure.

The chain growth step may utilize a neat aluminum alkyl medium or may utilize up to about 90 weight percent of a hydrocarbon solvent diluent such as xylene, cumene, toluene, pentane, hexane, heptane, octane, decene, and the like. Reaction temperature in the chain growth step may vary from approximately room temperature (20° C.) to 150° C. Pressures of ethylene employed in the chain growth step may vary from about 1 atmosphere to about 10 atmospheres.

Step 2 of the above process is generally conducted in the presence of a displacement catalyst using an excess of ethylene as the lower displacing olefin. The higher molecular weight aluminum alkyls, which would yield the desired olefins upon displacement, may be separated from the lower molecular weight aluminum alkyls prior to displacement. The separated lower molecular weight aluminum alkyls may optionally be recycled to chain growth conditions. The recycle may be immediate or may involve storage for a period of time. Mixing of the recycled trialkyl aluminum compounds with other feed materials such as ethylene, other trialkyl aluminum compounds, and chain growth catalyst is considered to be within the scope of this process. Typically, the desired displaced LAO's are in the range of $C_6$–$C_{30}$, preferably in the range of $C_6$–$C_{20}$, and most preferably in the range of $C_8$–$C_{16}$.

After or as part of the separation (Step 3 in the above process), the lower molecular weight aluminum alkyls may be recycled to chain growth conditions. Excess ethylene present as the displacing lower olefin may also be recycled to chain growth conditions. Further processing of the desired olefins, after displacement from the trialkyl aluminum compounds, is also considered to be within the scope of this process. Such further processing of the displaced olefins includes purification, separation, conversion to an alcohol, isomerization, oligomerization, polymerization, and combinations of the preceding.

The chain growth catalyst system of this disclosure comprises, in combination, an unbridged metallocene catalyst and a co-catalyst of cationic aluminum complexes having an amidinate ligand and inert anion. Unbridged metallocene compounds are known in the art and are used as a catalyst for polymerizing ethylene. Examples of unbridged metallocenes catalysts which have been used for polymerizing ethylene are given in Formula 1 below.

$$(C_p)_2MX_2 \qquad \text{Formula 1.}$$

These metallocenes consist of a metal atom (M) bound to two halogen atoms (X) and two cyclopentadienyl rings ($C_p$). In the above, M is a metal selected from the group consisting of titanium, zirconium, hafnium, thorium, and uranium. $C_p$ is a cyclopentadienyl ring which may be substituted, e.g., with a methyl or ethyl group replacing one of the hydrogens on the ring. For ethylene polymerization, these simple metallocenes are activated by co-catalysts such as methylaluminoxane (MAO).

Later, bridged metallocenes were developed. In bridged metallocenes, the cyclopentadienyl rings are linked by a chemical bridge. It was subsequently discovered that bridged metallocenes, when used in combination with a co-catalyst such as MAO, could polymerize propylene to highly isotactic polypropylene, highly syndiotactic polypropylene or atactic polypropylene, depending on the structure of the bridged metallocenes employed.

In this application, Applicants disclose the use of unbridged metallocenes, i.e., those encompassed by Formula 1, used in combination with a co-catalyst, such as an aluminum amidinate, as a catalyst system in the alkyl chain growth step of the process for LAO's described above. The preparation of these compounds is generally known in the art. For the process of this invention, a preferred metallocene is the one where $C_p$ is an ethyl substituted cyclopentadienyl ring, M is hafnium, and X is chlorine in Formula 1.

The aluminum amidinate co-catalysts of this invention, also employed in the chain growth step of the LAO process, are represented by Formula 2 below,

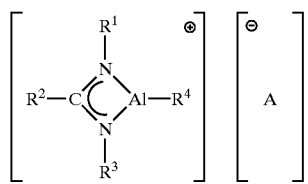

Formula 2 wherein $R^1$, $R^2$, $R^3$ and $R^4$ may be the same or different and are selected from the group consisting of $C_1$ to $C_{30}$ alkyl, cycloalkyl, and aryl groups. A is an anion which balances the charge of the aluminum cation. The required qualities of anion A are that it be inert toward reaction with the cationic catalyst, non-coordinating, bulky and unreactive toward the aluminum alkyl medium. In a preferred embodiment, $R^4$ is a methyl group and the anion, A, contains boron. In an especially preferred embodiment, $R^1$ and $R^3$ are each isopropyl groups, $R^4$ and $R^2$ are methyl groups and the anion, A, is $B(C_6F_5)_4^{-1}$, where $C_6F_5$ is a pentafluorophenyl group. Preparation of aluminum amidinates is disclosed, e.g., in U.S. Pat. No. 5,973,088 (Jordan et al.).

The use of aluminum amidinate catalyst improves the lifetime of the catalyst system. It is generally known by those skilled in this art area that activation cations such as N,N-dimethylanilinium and triphenylcarbenium react with trialkylaluminum compounds to form a highly electrophilic species often referred to as "$R_2Al^+$" which can attack and degrade inert counter-anions such as pentafluorophenylborate (see Bochman and Sarsfield *Organometallics* 1998, 17, 5908).

EXAMPLES 1–2

For both examples in this application, the metallocene employed was as given by Formula 1 above where $C_p$ is an ethyl substituted cyclopentadienyl ring, M is hafnium, and X is chlorine. Also, for both examples in this application, the aluminum amidinate co-catalyst employed was as given by Formula 2 above where $R^1$ and $R^3$ are each isopropyl groups, $R^2$ and $R^4$ are each methyl groups and the anion, A, is $B(C_6F_5)_4^{-1}$ where $C_6F_5$ is a pentafluorophenyl group. For Examples 1 and 2, the metallocene was deployed in approximately a 1 to 1 molar ratio with the aluminum amidinate, but molar ratios ranging from about 10 to 1 to about 1 to 10 are typical. Both components of the catalyst system were deployed from stock solutions which were about 0.006 to 0.01 Molar for the co-catalyst and the metallocene respectively, with toluene as the solvent.

For both examples, the triethylaluminum (TEA) was deployed neat. The metallocene was incubated in TEA at the temperatures and pressures shown in Table 1 for about 30 minutes prior to introduction of the co-catalyst. After introduction of the co-catalyst, an induction period was observed before uptake of ethylene. The induction period was about 30 minutes for Example 1 (80° C.) and about 2 minutes for Example 2 (100° C.).

The TEA was deployed in a molar ratio of about 3,300 to 1 to the catalyst composition but ratios ranging from 100,000 to 1 to 100 to 1 are typical. Each of the examples was permitted to react for 45 minutes and yielded a full range of trialkylaluminum compounds ranging from $C_4$ to $C_{30}$ alkyls. The trialkylaluminum products formed consisted of both homologous (all alkyl groups the same) and non-homologous (mixed alkyl groups). The amounts of each trialkylaluminum compound present were determined by conventional gas chromatographic techniques. Upon displacement of the grown alkyl groups from the trialkylaluminum compounds, the LAO product mix as indicated in Table 1 would have been obtained.

TABLE 1

| Linear Alpha Olefin Product | Wt % - Ex. No. 1 (80° C.) 80 psi (5.36 bar) $C_2H_4$ | Wt % - Ex. No. 2 (100° C.) 80 psi (5.36 bar) $C_2H_4$ |
|---|---|---|
| $C_4$ | 7.9 | no data |
| $C_6$ | 9.7 | 15.4 |
| $C_8$ | 11.6 | 15.4 |

TABLE 1-continued

| Linear Alpha Olefin Product | Wt % - Ex. No. 1 (80° C.) 80 psi (5.36 bar) $C_2H_4$ | Wt % - Ex. No. 2 (100° C.) 80 psi (5.36 bar) $C_2H_4$ |
|---|---|---|
| $C_{10}$ | 10.4 | 13.4 |
| $C_{12}$ | 9.7 | 11.8 |
| $C_{14}$ | 8.9 | 9.7 |
| $C_{16}$ | 7.4 | 8.7 |
| $C_{18}$ | 7.3 | 7.3 |
| $C_{20}$ | 6.4 | 6.4 |
| $C_{22}$ | 5.7 | 6.3 |
| $C_{24}$ | 4.3 | 4.9 |
| $C_{26}$ | 4.2 | 0.2 |
| $C_{28}$ | 3.2 | 0.2 |
| $C_{30}$ | 3.1 | 0.2 |

The data of Table 1 show that a full range of linear alpha olefin products may be prepared by the process of this invention.

Reasonable variation and modification are possible in the scope of the foregoing disclosure and the appended claims to this invention. The essence of this invention is a process for the preparation of an aluminum alkyl chain growth product by the chain growth reaction of alpha olefin on an aluminum alkyl, wherein the improvement comprises catalyzing the chain growth reaction with a catalyst system which comprises in combination (a) non-bridged metallocenes and (b) aluminum complexes having amidinate ligands and inert anions.

We claim:

1. A method of preparing a full range of $C_6$–$C_{30}$ linear alpha olefins by a process comprising the steps of:
   (1) growing ethylene onto a low molecular weight aluminum trialkyl so as to increase the carbon count of the alkyl groups of the aluminum trialkyls,
   (2) reacting said grown higher aluminum trialkyls with low molecular weight olefins to obtain a displacement of the higher molecular weight alkyl groups by said lower olefins thus forming higher olefins and lower molecular weight aluminum trialkyls corresponding to the displacing olefins, and
   (3) separating the desired displaced higher molecular weight olefins as product from the lower molecular weight aluminum alkyls and the remainder of the reaction mixture;

wherein the catalyst system for Step 1 comprises in combination non-bridged metallocenes as given by Formula 1 and aluminum complexes having amidinate ligands and inert anions as given by Formula 2, $(C_p)_2MX_2$   Formula 1

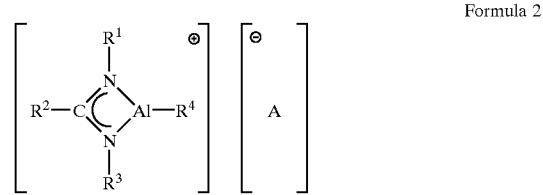

Formula 2 wherein M is a metal selected from the group consisting of titanium, zirconium, and hafnium, $C_p$ is a substituted or unsubstituted cyclopentadienyl ring, X is halogen, $R^1$, $R^2$, $R^3$ and $R^4$ may be the same or different and are selected from the group consisting of $C_1$ to $C_{30}$ alkyl, cycloalkyl, and aryl groups, and A is an inert anion which balances the charge of the aluminum cation.

2. The process of claim 1 wherein $C_p$ is an ethyl substituted cyclopentadienyl ring.

3. The process of claim 1 wherein M is hafnium.

4. The process of claim 1 wherein X is chlorine.

5. The process of claim 1 wherein $R^2$ and $R^4$ are each methyl groups.

6. The process of claim 1 wherein $R^1$ and $R^3$ are each isopropyl groups.

7. The process of claim 1 wherein anion A is comprised of boron.

8. The process of claim 7 wherein anion A is $B(C_6F_5)_4^{-1}$ and $C_6F_5$ is a pentafluorophenyl group.

9. The process of claim 1 wherein the low molecular weight olefin of Step 2 is ethylene.

* * * * *